US008852420B2

(12) United States Patent
Chang et al.

(10) Patent No.: US 8,852,420 B2
(45) Date of Patent: Oct. 7, 2014

(54) METHOD FOR CALIBRATING TEST METER BY BIOSENSOR TEST STRIP

(71) Applicant: DELBio, Inc., Taoyuan Hsien (TW)

(72) Inventors: Ching-Yu Chang, Taoyuan Hsien (TW); Hung-Ping Liu, Taoyuan Hsien (TW)

(73) Assignee: DELBio, Inc., Taoyuan Hsien (TW)

( * ) Notice: Subject to any disclaimer, the term of this patent is extended or adjusted under 35 U.S.C. 154(b) by 113 days.

(21) Appl. No.: 13/763,311

(22) Filed: Feb. 8, 2013

(65) Prior Publication Data

US 2013/0220839 A1  Aug. 29, 2013

Related U.S. Application Data

(60) Provisional application No. 61/597,277, filed on Feb. 10, 2012.

(51) Int. Cl.
*G01N 27/327* (2006.01)
*G01N 27/416* (2006.01)

(52) U.S. Cl.
CPC .......... *G01N 27/4163* (2013.01); *G01N 27/327* (2013.01)
USPC ...................................... 205/777.5; 205/792

(58) Field of Classification Search
CPC ............ G01N 27/327; G01N 27/3272; G01N 27/3273; G01N 27/4163
See application file for complete search history.

(56) References Cited

U.S. PATENT DOCUMENTS 6,827,829 B2 * 12/2004 Kawanaka et al. ...... 204/403.02
2010/0326824 A1 * 12/2010 Leong ........................ 204/406

* cited by examiner

*Primary Examiner* — Alexander Noguerola
(74) *Attorney, Agent, or Firm* — Muncy, Geissler, Olds & Lowe, P.C.

(57) ABSTRACT

A calibration method, including steps of: providing a test meter having a socket provided with a set of conductive pins; providing a biosensor test strip having a set of strip electrodes corresponding to the set of conductive pins, wherein the combination of lengths of the strip electrodes corresponds to a parameter code; inserting the biosensor test strip into the socket of the test meter so that each of the conductive pins and each of the corresponding strip electrode have a relative motion; reading out the parameter code by using a set of pulse widths detected by each of the conductive pins in the insertion period; and calibrating the test meter by using the parameter code to match a calibration parameter installed in the test meter.

15 Claims, 9 Drawing Sheets

METHOD FOR CALIBRATING TEST METER BY BIOSENSOR TEST STRIP

CROSS REFERENCE TO RELATED APPLICATIONS

This application claims the benefit of U.S. Provisional Application No. 61/597,277 filed on Feb. 10, 2012, the entirety of which is incorporated by reference herein.

BACKGROUND OF THE INVENTION

1. Field of the Invention

The present invention relates to a method for calibrating a test meter by a biosensor test strip, and in particular, relates to a method for calibrating a test meter by a biosensor test strip which reads out a parameter code and checks whether the biosensor test strip is completely inserted into the test meter by monitoring a pulse width variation.

2. Description of the Related Art

Tools for measuring the concentration of the substances in biological fluids are important for the diagnosis and help for treatment of many medical conditions. For, example, a glucose meter is a medical device for determining the approximate concentration of glucose in the blood.

Since test strips may vary from batch to batch, some glucose meters require the user to manually enter in a code found on the vial of test strips or on a chip that comes with the test strip. By entering the coding manually into the glucose meter, the meter will be calibrated to the batch of test strips. If this process is not carried out, the meter reading may be inaccurate. However, a user often forgets to check if the test meter is calibrated to the batch of the test strip. In this regard, some test strips contain the code information in the strip, so the test meter can read the code information for calibration after the test strip is inserted to the test meter. This auto-calibration method reduces the possibility of user error.

For auto-calibration related techniques, U.S. Pat. No. 7,601,299 discloses that two trace loops with their respective resistance are printed on a test strip, and the test meter measures the two resistances and obtains their ratio which corresponds to a batch code for calibration. However, there are some problems in this method. For example, the resistance per unit length is hard to control, the measurement for the resistances is not easy and consumes a lot of power, and an incorrect batch code may be read out if the user does not insert the test strip properly.

Thus, a method for calibrating a test meter by a biosensor test strip is needed that can detect the code information easily, with low power consumption, and check whether the test strip is completely inserted into the test meter.

BRIEF SUMMARY OF THE INVENTION

A detailed description is given in the following embodiments with reference to the accompanying drawings.

The invention provides a method for calibrating a test meter by a biosensor test strip, including steps of: providing the test meter having a socket provided with a set of conductive pins; providing the biosensor test strip having a set of strip electrodes corresponding to the set of conductive pins, wherein the combination of lengths of the strip electrodes corresponds to a parameter code; inserting the biosensor test strip into the socket of the test meter so that each of the conductive pins and each of the corresponding strip electrodes have a relative motion; reading out the parameter code by using a set of pulse widths detected by each of the conductive pins in the insertion period; and calibrating the test meter by using the parameter code to match a calibration parameter installed in the test meter.

In the above method, the step of reading out the parameter code further includes steps of: providing a first voltage level by a first conductive pin of the set of conductive pins, wherein the first conductive pin contacts with a first strip electrode of the set of strip electrodes; and detecting a plurality of second voltage levels of a plurality of second conductive pins of the set of conductive pins, wherein the plurality of second conductive pins contact with a plurality of second strip electrodes of the set of strip electrodes, respectively, wherein the first strip electrode has a first length and each of the plurality of second strip electrodes has a second length shorter than the first length, and the first strip electrode and the plurality of second strip electrodes are coupled to each other and extended from a plurality of positions, respectively, with the same distance to the insertion front end of the biosensor test strip The above method further includes: setting one of the plurality of the second electrodes as a reference electrode which has a length independent from the parameter code.

The above method further includes: setting the pulse width detected by the second conductive pin in contact with the reference electrode as a reference value; normalizing the pulse widths detected by the other second conductive pins by the reference value; and acquiring the parameter code from the normalized pulse widths.

The above method further includes: providing a transverse electrode extending from the contact endpoint of the first strip electrode and not connected to the contact endpoints of the plurality of second strip electrodes, wherein the transverse electrode is in contact with all of the plurality of the conductive pins when the biosensor test strip is completely inserted into the test meter.

The above method further includes: detecting whether the second voltage levels of all of the plurality of second conductive pins have shifted to the first voltage level simultaneously during the insertion period to confirm that the biosensor test strip has been completely inserted.

The above method further includes: providing a first transverse electrode extending from the contact start point of the first strip electrode and not connected to the contact start points of the plurality of second strip electrodes, wherein the transverse electrode is in contact with all of the plurality of the conductive pins when the biosensor test strip is just inserted into the test meter, and the width of the first transverse electrode is a known constant.

The above method further includes: detecting the initial pulse widths of all of the plurality of second conductive pins during the insertion period to estimate the insertion speed of the biosensor test strip, and determining a sampling frequency of the plurality of the conductive pins according to the insertion speed.

The above method further includes: providing a second transverse electrode extending from the contact endpoint of the first strip electrode and not connected to the contact endpoints of the plurality of second strip electrodes, wherein the second transverse electrode is in contact with all of the plurality of the conductive pins when the biosensor test strip is completely inserted into the test meter.

The above method further includes: detecting whether the second voltage levels of all of the plurality of second conductive pins have shifted to the first voltage level simultaneously during the insertion period to confirm that the biosensor test strip has been completely inserted.

In the above method, the plurality of the strip electrodes are formed on a surface of the biosensor test strip, wherein the surface is opposite to a reagent carrying surface.

The invention also provides a method for calibrating a test meter by a biosensor test strip, including steps of: forming a plurality of strip electrodes on a surface of a biosensor test strip, wherein the pattern of the plurality of strip electrodes corresponds to a parameter code; inserting the biosensor test strip into a test meter to make the plurality of strip electrodes and corresponding conductive pins of the test meter have a relative motion; reading out the parameter code according to the pulse width variation recorded by the conductive pins during the process of the relative motion; and calibrating the test meter by using the parameter code to match a calibration parameter installed in the test meter.

The above method further includes: designing the pattern of the plurality of strip electrodes so that each of the conductive pins will receive a predetermined pulse width variation when the biosensor test strip is completely inserted into the test meter; and confirming that the biosensor test strip has been completely inserted according to the predetermined pulse width variation.

The above method further includes: designing the pattern of the plurality of strip electrodes so that each of the conductive pins will receive a predetermined pulse width variation when the biosensor test strip is just inserted into the test meter; estimating the insertion speed of the biosensor test strip according to the predetermined pulse width variation; and determining a sampling frequency of the conductive pins according to the insertion speed.

The above method further includes: designing the pattern of the plurality of strip electrodes so that each of the conductive pins will receive a second predetermined pulse width variation when the biosensor test strip is completely inserted into the test meter; and confirming that the biosensor test strip has been completely inserted according to the second predetermined pulse width variation.

According to the methods for calibrating a test meter by a biosensor test strip, the code information written on the biosensor test strip can be read out easily, with low power consumption. The state where the test strip is completely inserted into the test meter can be ensured. The sampling rate can be dynamically adjusted to reduce the required capacity of the memory.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
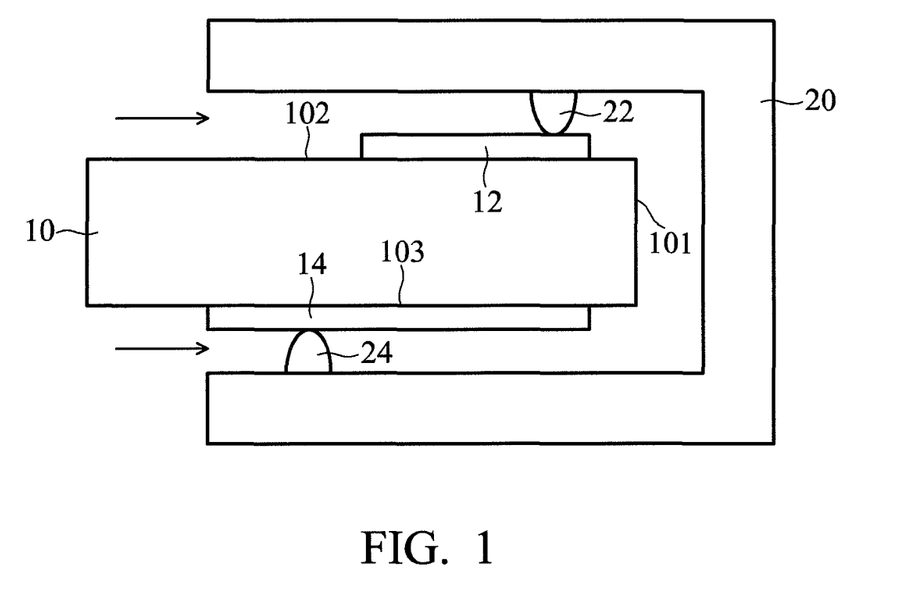
FIG. 1 is a schematic section view of a biosensor test strip and a socket of a test meter in accordance with the invention.

FIG. 1 is a schematic section view of a biosensor test strip and a socket of a test meter in accordance with the invention. As shown in FIG. 1, a biosensor test strip 10 is inserted into a socket 20 of a test meter. The biosensor test strip 10 comprises at least a set of reaction electrodes 12 on its top surface 102 and a plurality of strip electrodes 14 on its bottom surface 103. The socket 20 comprises top conductive pins 22 and bottom conductive pins 24. When the biosensor test strip 10 is inserted into the socket 20, the reaction electrodes 12 and the strip electrodes 14 contact with the top conductive pins 22 and the bottom conductive pins 24, respectively. The reaction electrodes 12 are used for transmitting the electric current generated by the chemical reaction between the sample and the reagent. On the other hand, the pattern of the strip electrodes 14 corresponds to a parameter code that the test meter reads for calibration. In the present invention, the relative motion between any one of the strip electrodes 14 and the corresponding bottom conductive pin 24 during the insertion period will generate pulse width variation. The test meter then obtains the parameter code by measuring the pulse width.

Figure 2:
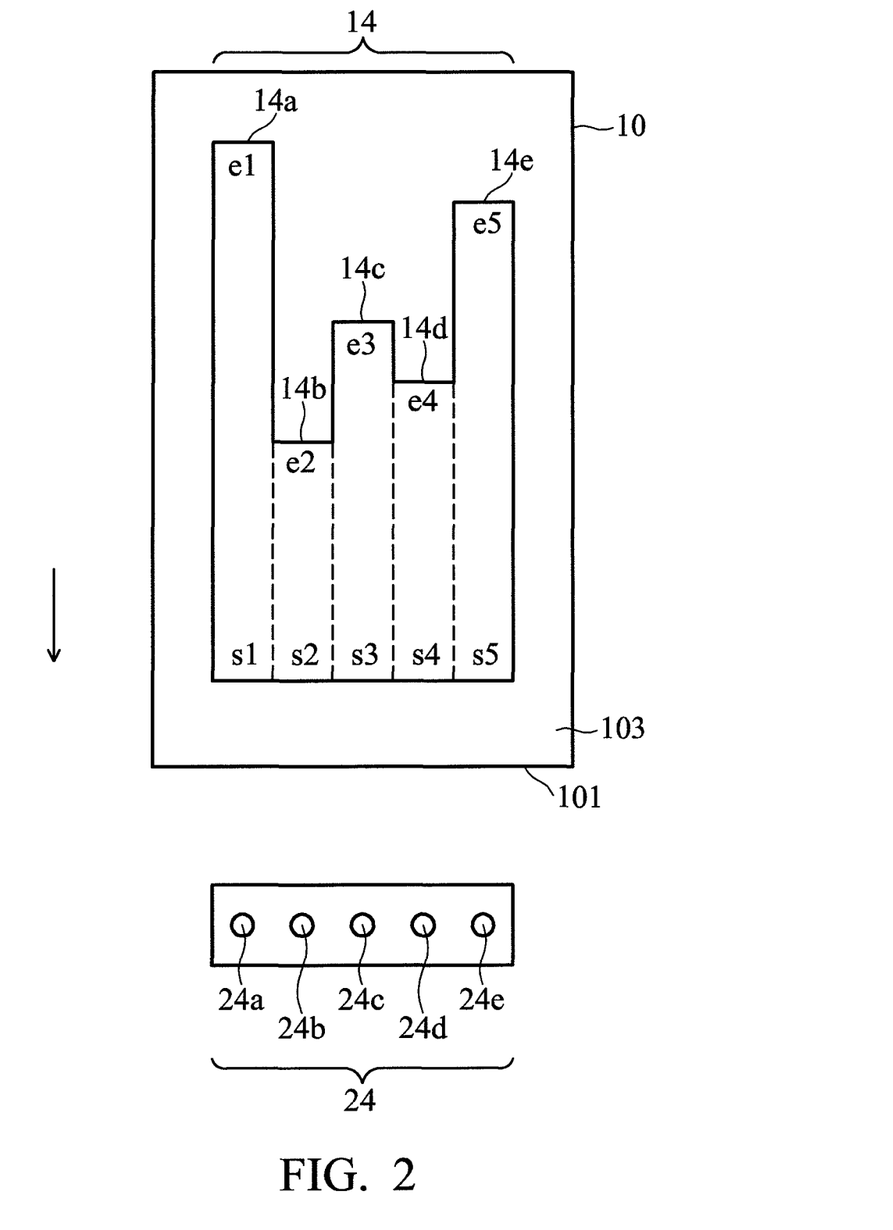
FIG. 2 is a schematic plan view of a biosensor test strip provided with a strip electrode pattern in accordance with a first embodiment of the invention.

FIG. 2 is a schematic plan view of a biosensor test strip provided with a strip electrode pattern in accordance with a first embodiment of the invention. As shown in FIG. 2, a plurality of strip electrodes 14 comprising strip electrodes 14a-14e are formed on the bottom surface 10 of the biosensor test strip 10, and the bottom conductive pins 24 comprise conductive pins 24a-24e. The strip electrodes 14a-14e have their own lengths, respectively, and are coupled together at least at their contact start points s1-s5. The contact start points s1-s5 have the same distance to the insertion front end 101 of the biosensor test strip 10. Therefore, when the biosensor test strip 10 is inserted into the socket 20 of the test meter, the strip electrodes 14a-14e are in contact with the corresponding conductive pins 24a-24e simultaneously. In the insertion process, because strip electrodes 14a-14e having different lengths are arranged on the moving path for the conductive pins 24a-24e, the contact time periods of the conductive pins 24a-24e and the strip electrodes 14a-14e are different accordingly.

In the structure shown in FIG. 2, the strip electrode 14a has a longest length which allows the strip electrode 14a contact with the conductive pins 24a continuously in the entire insertion period. When the insertion is finished, the conductive pins 24a stops at the contact endpoint e1 of the strip electrode 14a. Therefore, the test meter outputs a high voltage level via the conductive pins 24a to the strip electrode 14a coupled to the other strip electrodes 14b-14e, so that the strip electrodes 14a-14e are all at the high voltage level in the entire insertion period. The conductive pins 24b-24e are used for detecting voltage levels. The conductive pin 24b is at the high voltage level when located between the contact start point s2 and the contact endpoint e2 of the strip electrode 14b, and at a low voltage level when located behind the contact endpoint e2 of the strip electrode 14b. The conductive pin 24c is at the high voltage level when located between the contact start point s3 and the contact endpoint e3 of the strip electrode 14c, and at the low voltage level when locating behind the contact endpoint e3 of the strip electrode 14c. The conductive pin 24d is at the high voltage level when located between the contact start point s4 and the contact endpoint e4 of the strip electrode 14d, and at the low voltage level when locating behind the contact endpoint e4 of the strip electrode 14d. The conductive pin 24e is at the high voltage level when located between the contact start point s5 and the contact endpoint e5 of the strip electrode 14e, and at a low voltage level when locating behind the contact endpoint e5 of the strip electrode 14e. In this way, the conductive pins 24b-24e detect different pulse widths in proportions to the lengths of the strip electrodes 14b-14e.

Figure 3:
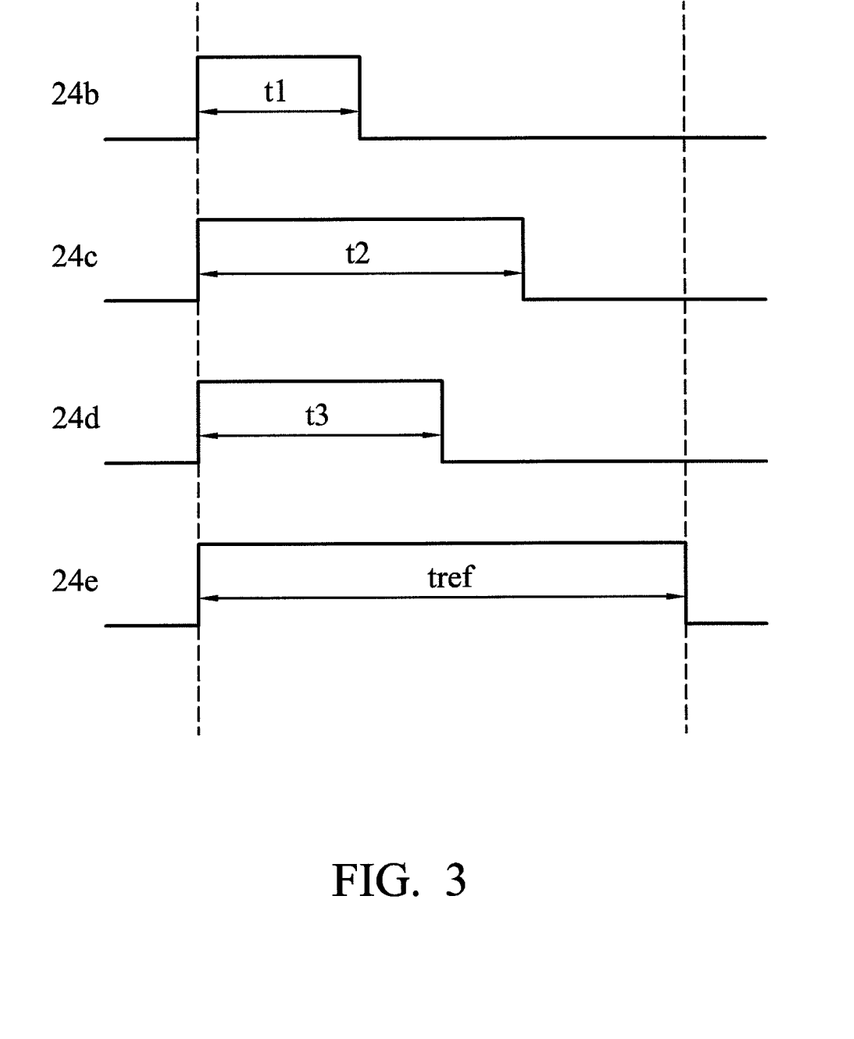
FIG. 3 is a diagram showing the voltage levels of bottom conductive pins in the insertion period in accordance with the first embodiment.

FIG. 3 is a diagram showing the voltage levels of bottom conductive pins in the insertion period in accordance with the first embodiment. In this embodiment, the strip electrode 14e is used as a reference electrode. This means the length of the strip electrode 14e is the same for different batches of the biosensor test strips. Therefore, as shown in FIG. 3, the pulse width detected by the conductive pin 24e is taken as a reference value $t_{ref}$. If the length of the strip electrode 14e is known in advance by the test meter, the test meter can calculate the lengths of the strip electrodes 14b-14d by comparing the pulse widths t1-t3 detected by the conductive pins 24b-24d to the reference value $t_{ref}$. According to the lengths of the strip electrodes 14b-14d, a corresponding parameter code can be read out. If the length of the strip electrode 14e is unknown to the test meter, the test meter can just normalize the pulse widths t1-t3 by the reference value $t_{ref}$. According to the normalized pulse widths $1/t_{ref}$, $t2/t_{ref}$, and $t3/t_{ref}$, a corresponding parameter code can also be read out. As a result, the parameter code is used to match a calibration parameter installed in the test meter, and the test meter is then calibrated by the calibration parameter.

According to the first embodiment, the parameter code is read out according to the pulse widths t1-t3. Therefore, in comparison to detecting the resistance, detecting a time period is easy and accurate. The digital measuring can also prevent influence of noise. Further, the lengths of the strip electrodes 14b-14d can have many combinations. Therefore, the number of parameter codes that corresponds to different batches is increased.

Figure 4:
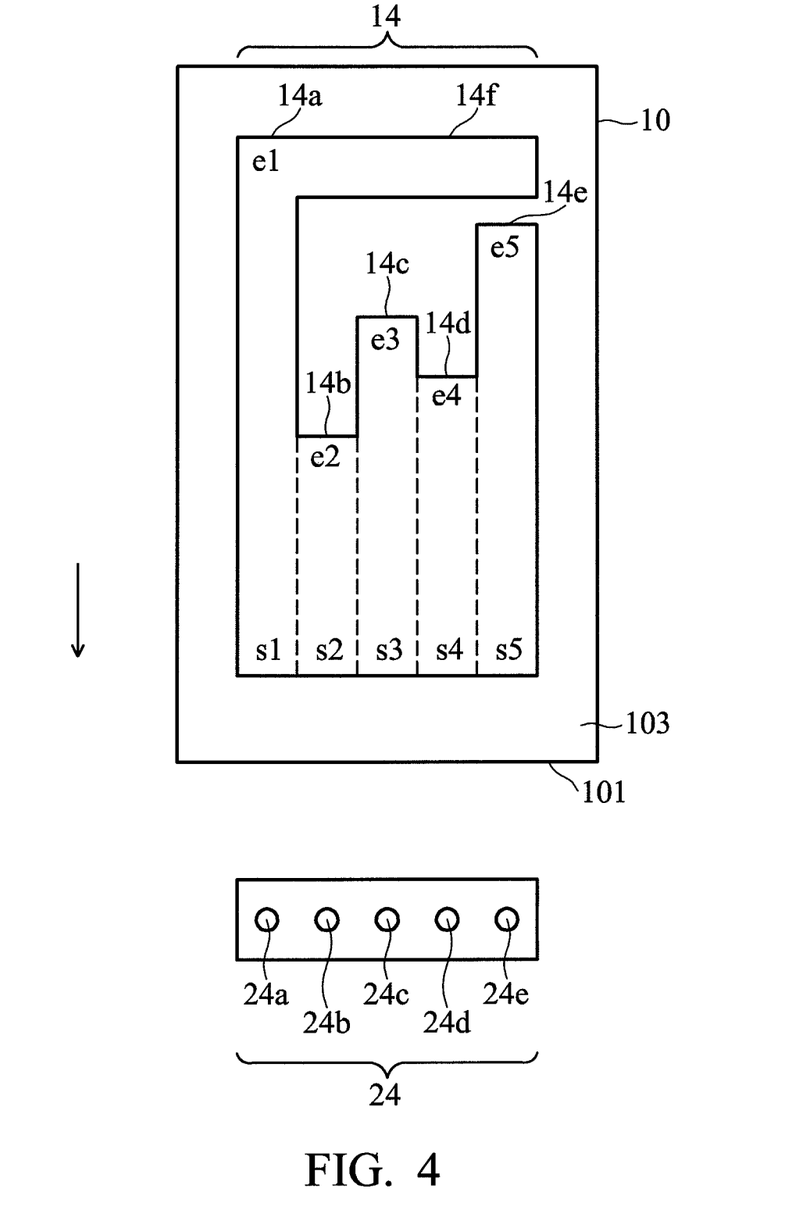
FIG. 4 is a schematic plan view of a biosensor test strip provided with a strip electrode pattern in accordance with a second embodiment of the invention.

FIG. 4 is a schematic plan view of a biosensor test strip provided with a strip electrode pattern in accordance with a second embodiment of the invention. In the insertion process, the user sometimes doesn't push the biosensor test strip 10 to the end, resulting in an incorrect measurement or calibration. In order to check whether the biosensor test strip 10 is completely inserted into the socket 20 of the test meter, the strip electrodes 14 can be formed as shown in FIG. 4. The strip electrodes 14 further comprises a strip electrode 14f extending along the test strip width direction from the contact endpoint e1 of the strip electrode 14a. The strip electrode 14f is not connected to the contact endpoints e2-e5 of the strip electrodes 14b-14e. In this structure, when the biosensor test strip 10 is completely inserted into the socket 20 of the test meter, all the conductive pins 24a-24e stop on the strip electrode 14f.

Figure 5:
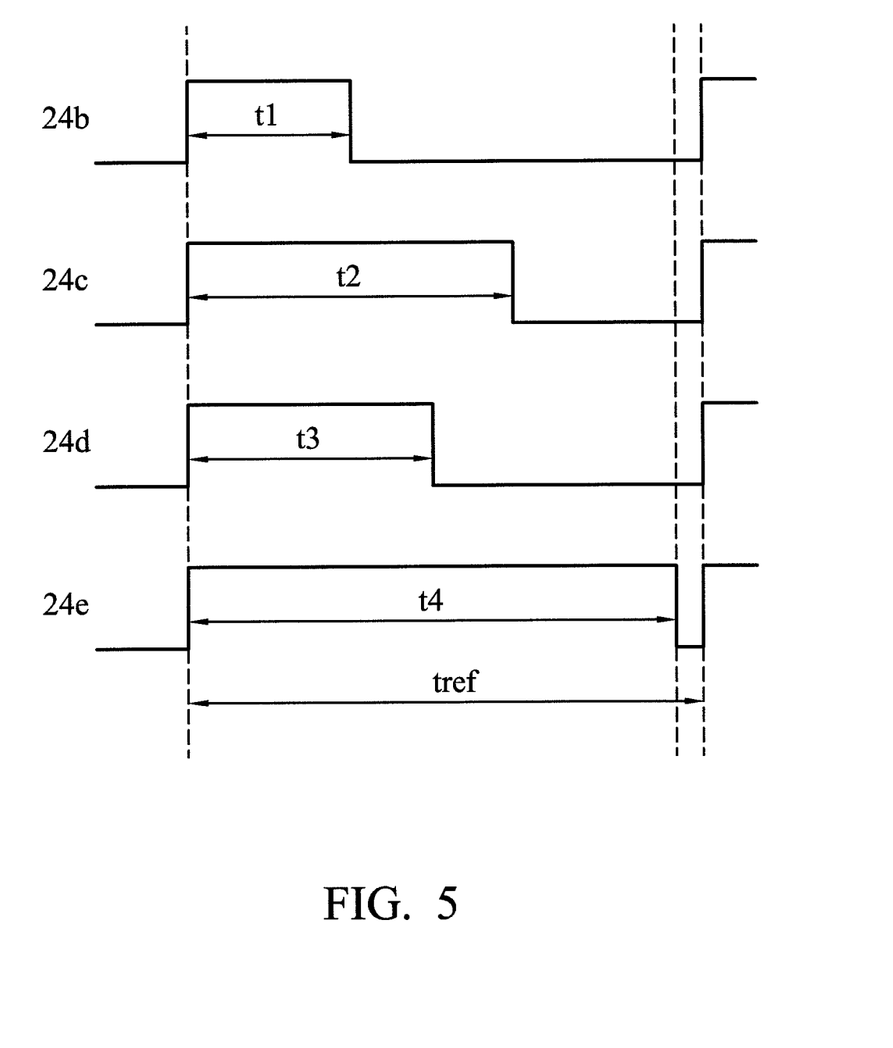
FIG. 5 is a diagram showing the voltage levels of bottom conductive pins in the insertion period in accordance with the second embodiment.

FIG. 5 is a diagram showing the voltage levels of bottom conductive pins in the insertion period in accordance with the second embodiment. As shown in FIG. 5, because the conductive pins 24b-24e stop on the strip electrode 14f when the insertion is correctly finished, the conductive pins 24b-24e are all at the high voltage level eventually. Therefore, by checking that the voltage levels of the conductive pins 24b-24e have shifted to the high voltage level simultaneously again, the state where the biosensor test strip 10 has been completely inserted into the test meter can be confirmed. If the biosensor test strip 10 is not completely inserted into the test meter, the test meter can send out a warning signal, such as a message displayed on the screen of the test meter, to warn the user of the incorrect insertion.

According to the second embodiment, the state where the biosensor test strip 10 has been completely inserted into the socket 20 of the test meter can be confirmed according to a predetermined pulse width variation. Further, the time period between the first rising edge and the second rising edge of a waveform detected by any one of the conductive pins 24b-24e rather than the pulse width t4 detected by the conductive pin 24e can be taken as a reference value $t_{ref}$. The length of the strip electrode 14e can also join in the coding for the parameter code. Therefore, the number of combination of parameter codes is further increased.

Figure 6:
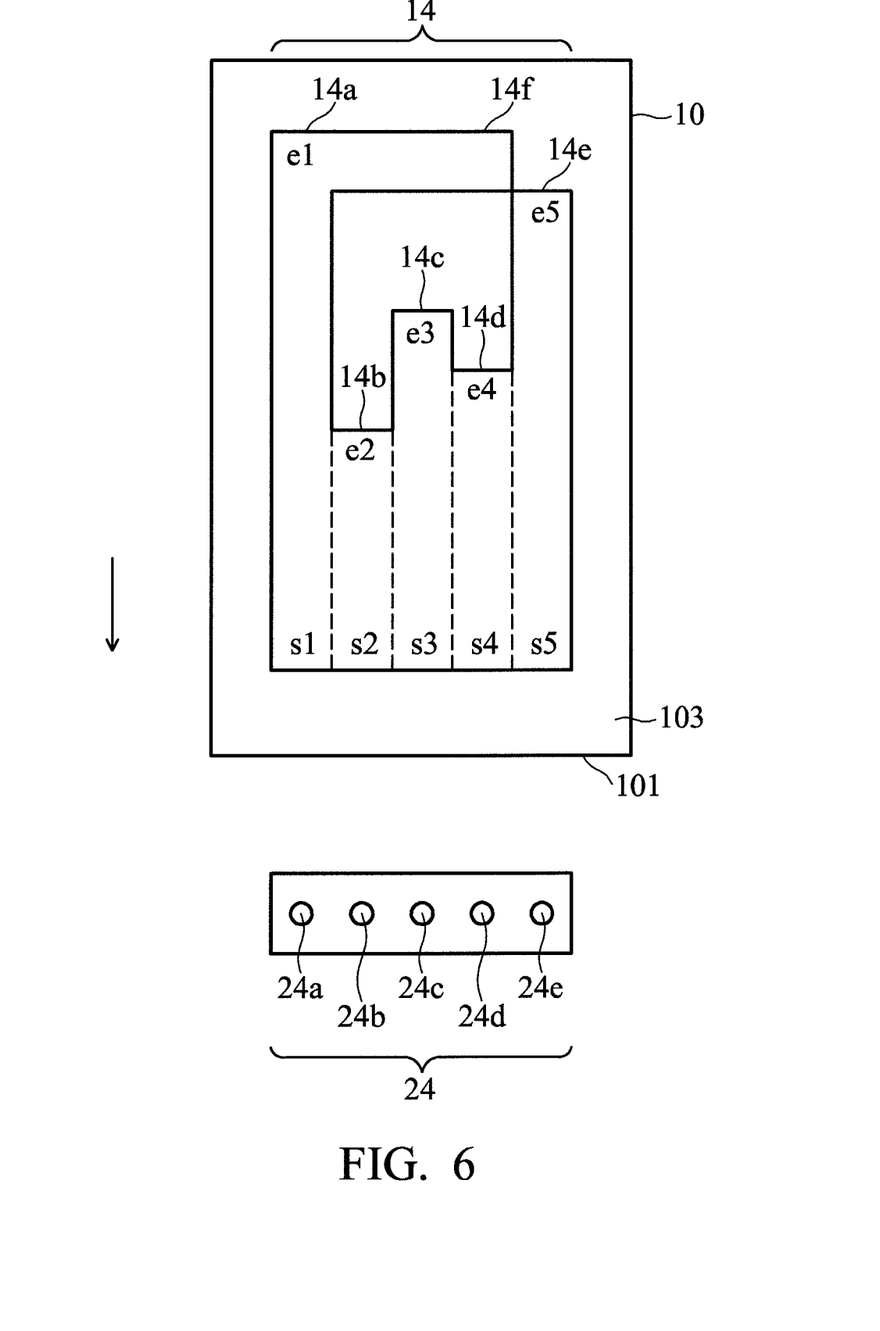
FIG. 6 is a schematic plan view of a biosensor test strip provided with a strip electrode pattern in accordance with a modification of the second embodiment of the invention.

However, the strip electrode 14f is not limited to the pattern shown in FIG. 4. For example, the strip electrode 14f can be shorter than that shown in FIG. 4. FIG. 6 is a schematic plan view of a biosensor test strip provided with a strip electrode pattern in accordance with a modification of the second embodiment of the invention. As shown in FIG. 6, the strip electrode 14f only extends on the path of the conductive pins 24b-24d. Therefore, when the biosensor test strip 10 is completely inserted into the socket 20 of the test meter, only the conductive pins 24a-24d stop on the strip electrode 14f. In this structure, when the insertion is finished correctly, the conductive pins 24b-24d are at the high level and the conductive pin 24e is at the low voltage level. That is to say, as long as at least one of the conductive pins 24b-24e is shifted to the high voltage level again when the insertion is finished correctly, there are many kinds of variations to design the strip electrode 14f for checking whether the biosensor test strip 10 is correctly inserted into the socket 20 of the test meter.

In addition, different users may insert the biosensor test strip into the test meter at different insertion speed, resulting in that the reference values $t_{ref}$ are not the same. If the insertion speed is too low, the reference value $t_{ref}$ becomes much longer than usual. Under a constant sampling rate for the conductive pins 24b-24e to detect the pulse width variation, the capacity of memory for storing the voltage level in each sampling should be increased. This will increase the cost of the test meter. In consideration of the issue, the present invention also provides a method to detect the insertion speed of the biosensor strip and then dynamically adjust the sampling rate for the conductive pins to decrease the required capacity of the memory.

Figure 7:
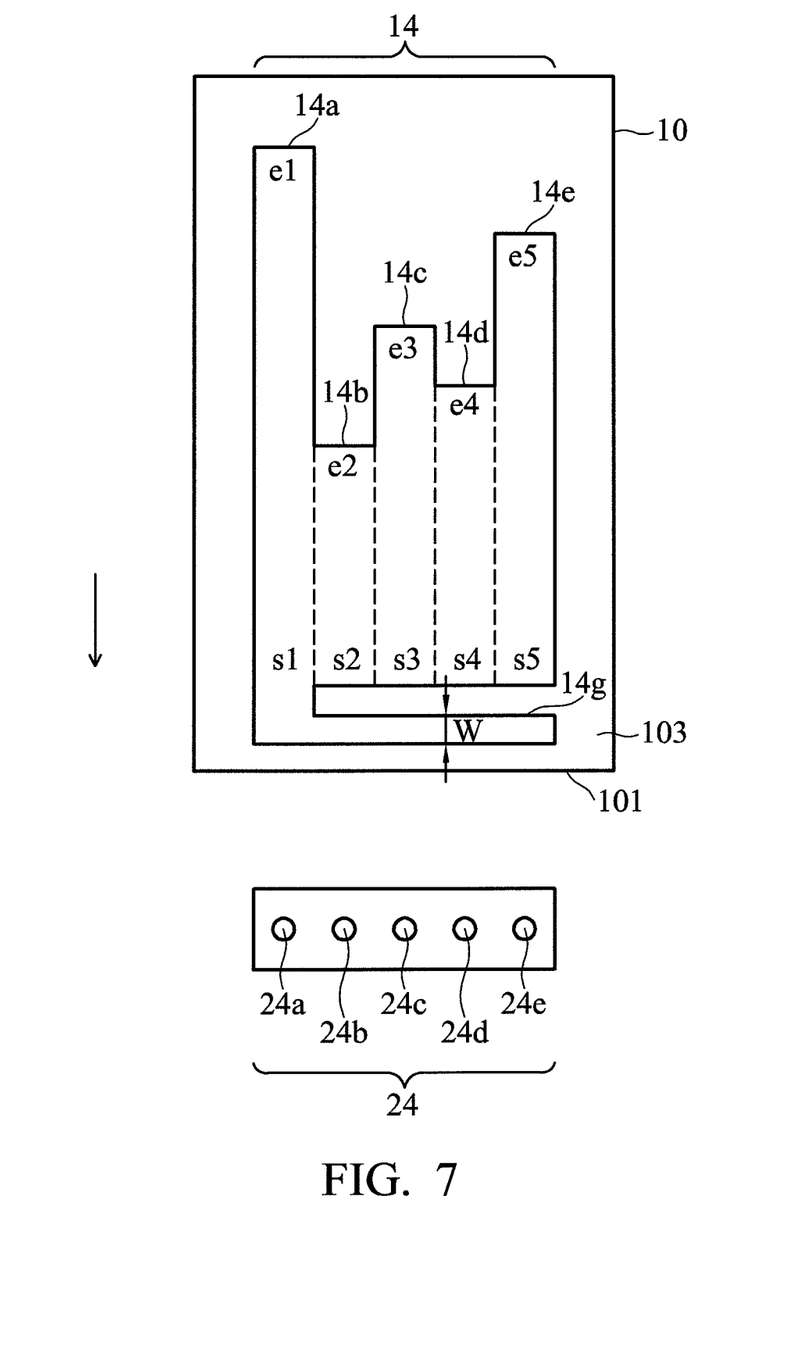
FIG. 7 is a schematic plan view of a biosensor test strip provided with a strip electrode pattern in accordance with a third embodiment of the invention.
Figure 8:
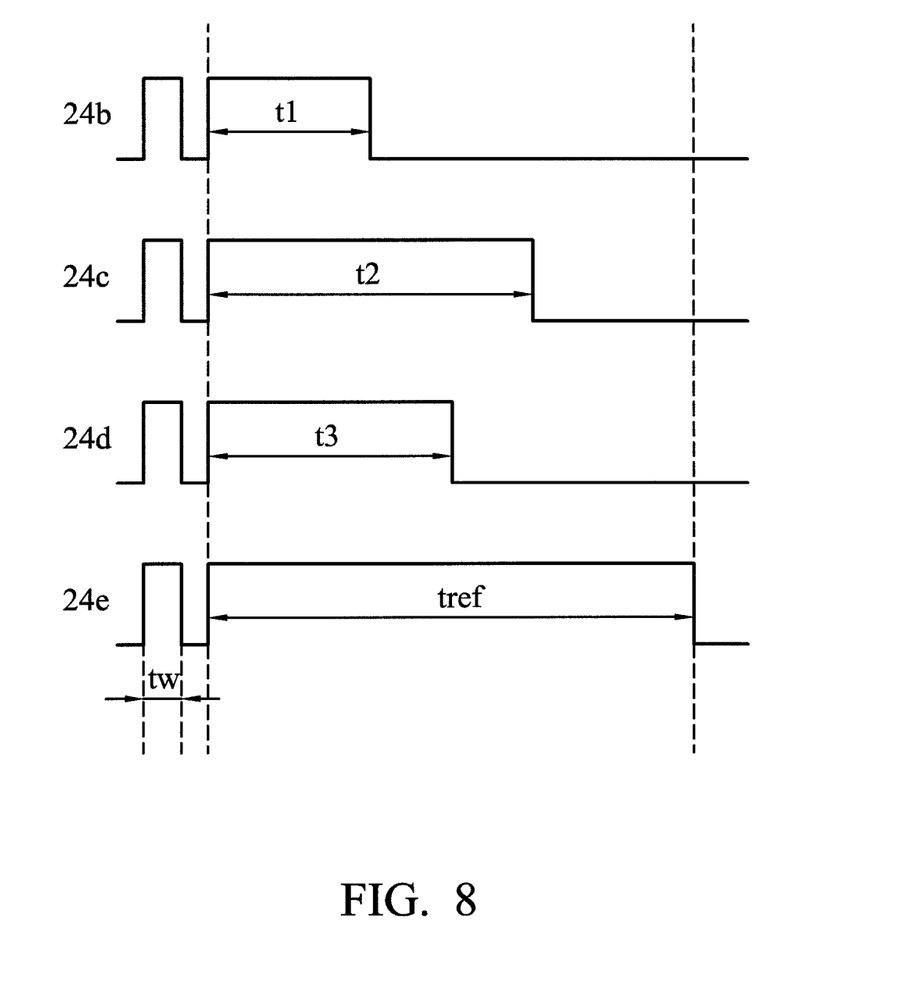
FIG. 8 is a diagram showing the voltage levels of bottom conductive pins in the insertion period in accordance with the third embodiment.

FIG. 7 is a schematic plan view of a biosensor test strip provided with a strip electrode pattern in accordance with a third embodiment of the invention. FIG. 8 is a diagram showing the voltage levels of bottom conductive pins in the insertion period in accordance with the third embodiment. In order to detect the insertion speed, the strip electrodes 14 can be formed as shown in FIG. 7. The strip electrodes 14 further comprise a strip electrode 14g extending from the contact start point s1 of the strip electrode 14a toward the insertion front end 101 of the biosensor test strip 10 and then extending in the test strip width direction. The strip electrode 14g is not connected to the contact start points s2-s5 of the strip electrodes 14b-14e. The strip electrode 14g has a known width w. When the biosensor test strip 10 is inserted to the socket 20 of the test meter, the conductive pins 24a-24e will pass through the strip electrode 14g before arriving at the start points s1-s5. Therefore, the conductive pins 24b-24e can detect the pulse width tw shown in FIG. 8 to calculate the insertion speed. According to the insertion speed, the reference value $t_{ref}$ can be estimated. Then the estimated reference value $t_{ref}$ and the capacity of the memory can used to determine a proper sampling rate for the conductive pins 24b-24e.

According to the third embodiment, the sampling rate for the conductive pins 24b-24e can be dynamically adjusted. Therefore, the required capacity of the memory can be reduced even though the insertion speed is low.

Figure 9:
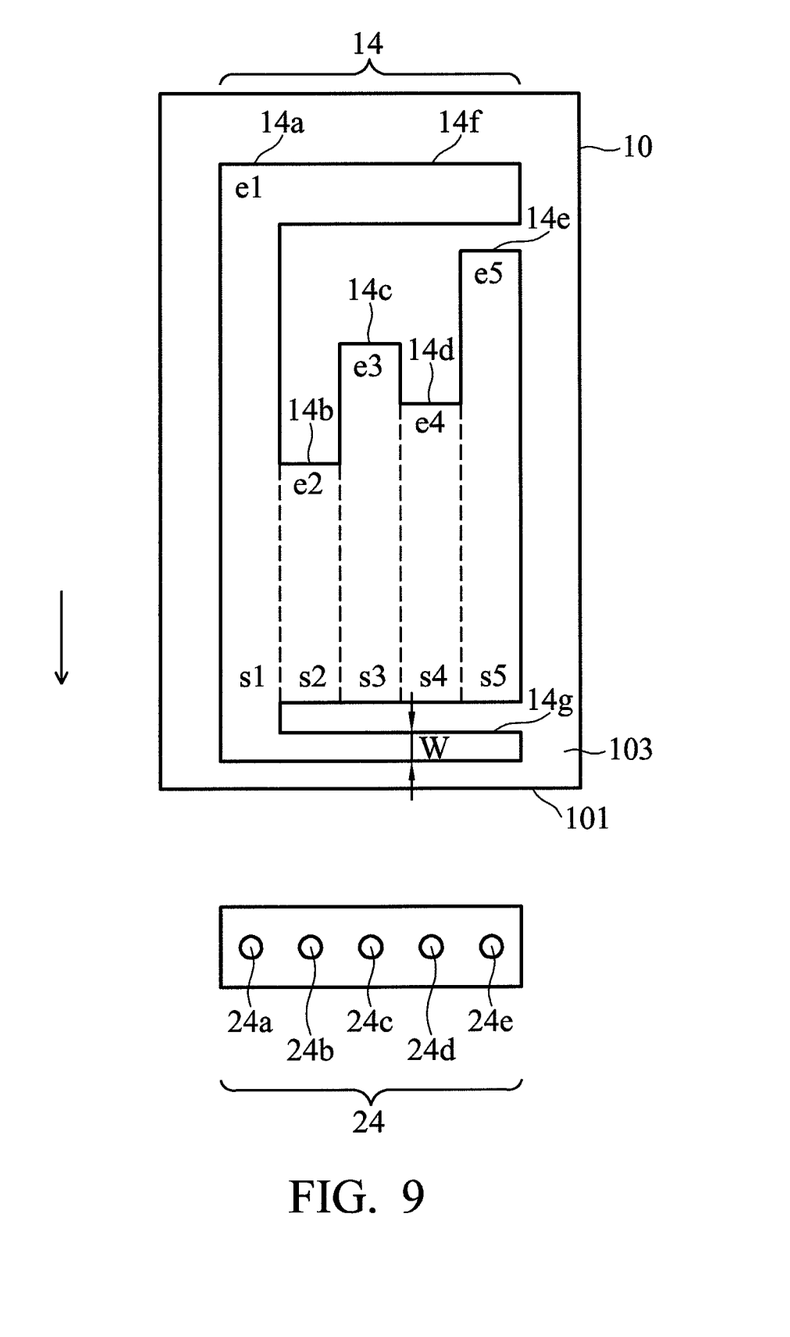
FIG. 9 is a schematic plan view of a biosensor test strip provided with a strip electrode pattern in accordance with a fourth embodiment of the invention.

Furthermore, the features of the second embodiment and third embodiment can be combined. FIG. 9 is a schematic plan view of a biosensor test strip provided with a strip electrode pattern in accordance with a fourth embodiment of the invention. The strip electrodes 14 have both the strip electrode 14f for checking whether the insertion is finished correctly, and the strip electrode 14g for calculating the insertion speed and adjusting the sampling rate.

According to the above embodiments, a method for calibrating a test meter by a biosensor test strip is provided which can detect the code information easily, with low power consumption, check whether the test strip is completely inserted into the test meter, and dynamically adjust the sampling rate to reduce the required capacity of the memory.

While the invention has been described by way of example and in terms of the preferred embodiments, it is to be understood that the invention is not limited to the disclosed embodiments. For example, the number of the strip electrodes is not limited to 5, or the reference electrode is not limited to the strip electrode 14e, etc. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for calibrating a test meter by a biosensor test strip, comprising steps of:
   providing the test meter having a socket provided with a set of conductive pins;
   providing the biosensor test strip having a set of strip electrodes corresponding to the set of conductive pins, wherein the combination of lengths of the strip electrodes corresponds to a parameter code;
   inserting the biosensor test strip into the socket of the test meter so that each of the conductive pins and each of the corresponding strip electrodes have a relative motion;
   reading out the parameter code by using a set of pulse widths detected by each of the conductive pins in the insertion period; and
   calibrating the test meter by using the parameter code to match a calibration parameter installed in the test meter.

2. The method as claimed in claim 1, wherein the step of reading out the parameter code further comprises steps of:
   providing a first voltage level by a first conductive pin of the set of conductive pins, wherein the first conductive pin contacts with a first strip electrode of the set of strip electrodes; and
   detecting a plurality of second voltage levels of a plurality of second conductive pins of the set of conductive pins, wherein the plurality of second conductive pins contact with a plurality of second strip electrodes of the set of strip electrodes, respectively,
   wherein the first strip electrode has a first length and each of the plurality of second strip electrodes has a second length shorter than the first length, and the first strip electrode and the plurality of second strip electrodes are coupled to each other and extended from a plurality of positions, respectively, with the same distance to the insertion front end of the biosensor test strip.

3. The method as claimed in claim 2, further comprising:
   setting one of the plurality of the second strip electrodes as a reference electrode which has a length independent from the parameter code.

4. The method as claimed in claim 3, further comprising:
   setting the pulse width detected by the second conductive pin in contact with the reference electrode as a reference value;
   normalizing the pulse widths detected by the other second conductive pins by the reference value; and
   acquiring the parameter code from the normalized pulse widths.

5. The method as claimed in claim 2, further comprising:
   providing a transverse electrode extending from the contact endpoint of the first strip electrode and not connected to the contact endpoints of the plurality of second strip electrodes, wherein the transverse electrode is in contact with all of the plurality of the conductive pins when the biosensor test strip is completely inserted into the test meter.

6. The method as claimed in claim 5, further comprising:
   detecting whether the second voltage levels of all of the plurality of second conductive pins have shifted to the first voltage level simultaneously during the insertion period to confirm that the biosensor test strip has been completely inserted.

7. The method as claimed in claim 2, further comprising:
   providing a first transverse electrode extending from the contact start point of the first strip electrode and not connected to the contact start points of the plurality of second strip electrodes, wherein the first transverse electrode is in contact with all of the plurality of the conductive pins when the biosensor test strip is just inserted into the test meter, and the width of the first transverse electrode is a known constant.

8. The method as claimed in claim 7, further comprising:
   detecting the initial pulse widths of all of the plurality of second conductive pins during the insertion period to estimate the insertion speed of the biosensor test strip, and
   determining a sampling frequency of the plurality of the conductive pins according to the insertion speed.

9. The method as claimed in claim 7, further comprising:
   providing a second transverse electrode extending from the contact endpoint of the first strip electrode and not connected to the contact endpoints of the plurality of second strip electrodes, wherein the second transverse electrode is in contact with all of the plurality of the conductive pins when the biosensor test strip is completely inserted into the test meter.

10. The method as claimed in claim 9, further comprising:
    detecting whether the second voltage levels of all of the plurality of second conductive pins have shifted to the first voltage level simultaneously during the insertion period to confirm that the biosensor test strip has been completely inserted.

11. The method as claimed in claim 1, wherein the plurality of the strip electrodes are formed on a surface of the biosensor test strip, wherein the surface is opposite to a reagent carrying surface.

12. A method for calibrating a test meter by a biosensor test strip, comprising steps of:
- forming a plurality of strip electrodes on a surface of a biosensor test strip, wherein the pattern of the plurality of strip electrodes corresponds to a parameter code;
- inserting the biosensor test strip into a test meter to make the plurality of strip electrodes and corresponding conductive pins of the test meter have a relative motion;
- reading out the parameter code according to the pulse width variation recorded by the conductive pins during the relative motion; and
- calibrating the test meter by using the parameter code to match a calibration parameter installed in the test meter.

13. The method as claimed in claim 12, further comprising:
- designing the pattern of the plurality of strip electrodes so that each of the conductive pins will receive a predetermined pulse width variation when the biosensor test strip is completely inserted into the test meter; and
- confirming that the biosensor test strip has been completely inserted according to the predetermined pulse width variation.

14. The method as claimed in claim 12, further comprising:
- designing the pattern of the plurality of strip electrodes so that each of the conductive pins will receive a first predetermined pulse width variation when the biosensor test strip is just inserted into the test meter;
- estimating the insertion speed of the biosensor test strip according to the first predetermined pulse width variation; and
- determining a sampling frequency of the conductive pins according to the insertion speed.

15. The method as claimed in claim 14, further comprising:
- designing the pattern of the plurality of strip electrodes so that each of the conductive pins will receive a second predetermined pulse width variation when the biosensor test strip is completely inserted into the test meter; and
- confirming that the biosensor test strip has been completely inserted according to the second predetermined pulse width variation.

* * * * *